United States Patent
Mauger

(10) Patent No.: US 9,716,952 B2
(45) Date of Patent: Jul. 25, 2017

(54) SOUND PROCESSING IN A HEARING DEVICE USING EXTERNALLY AND INTERNALLY RECEIVED SOUNDS

(71) Applicant: Stefan Mauger, Melbourne (AU)

(72) Inventor: Stefan Mauger, Melbourne (AU)

(73) Assignee: Cochlear Limited, Macquarie University (AU)

(*) Notice: Subject to any disclaimer, the term of this patent is extended or adjusted under 35 U.S.C. 154(b) by 0 days.

(21) Appl. No.: 14/863,686

(22) Filed: Sep. 24, 2015

(65) Prior Publication Data

US 2016/0119724 A1    Apr. 28, 2016

Related U.S. Application Data

(60) Provisional application No. 62/068,048, filed on Oct. 24, 2014.

(51) Int. Cl.
*H04R 25/00* (2006.01)
*A61N 1/36* (2006.01)
(Continued)

(52) U.S. Cl.
CPC ....... *H04R 25/505* (2013.01); *A61N 1/36032* (2013.01); *G10L 21/0264* (2013.01);
(Continued)

(58) Field of Classification Search
CPC .............. H04R 25/505; H04R 2225/43; H04R 2225/67; G10L 21/0264; G10L 21/0216; G10L 2021/02165; A61N 1/36032
See application file for complete search history.

(56) References Cited

U.S. PATENT DOCUMENTS

| | | | | |
|---|---|---|---|---|
| 2009/0016542 A1* | 1/2009 | Goldstein | ............. | H04R 3/005 381/57 |
| 2011/0098785 A1* | 4/2011 | Mishra | ............... | A61N 1/36032 607/57 |

(Continued)

OTHER PUBLICATIONS

K. Chung, Challenges and Recent Developments in Hearing Aids Part I. Speech Understanding in Noise, Microphone Technologies and Noise Reduction Algorithms, Trends Amplif, 2004, 83-124, vol. 8, No. 3.

(Continued)

*Primary Examiner* — Catherine Voorhees
(74) *Attorney, Agent, or Firm* — McDonnell Boehnen Hulbert & Berghoff LLP

(57) ABSTRACT

Disclosed herein are methods, systems, and devices for mitigating the impact of noise, such a low-frequency noise caused by wind, on sounds received at a hearing prosthesis. An example method includes receiving an external sound signal transduced externally to a recipient from an ambient sound and an internal sound signal transduced internally to the recipient from the ambient sound. The example method also includes determining that a triggering condition is present in the external sound signal. The triggering condition may be indicative of a condition in that more adversely affects externally-received sounds than internally-received sounds. In response to determining that the triggering condition is present in the external sound signal, the example method further includes generating a stimulation signal that is based at least in part on spectral information of the internally-transduced sound.

24 Claims, 6 Drawing Sheets

(51) Int. Cl.
*G10L 21/0264* (2013.01)
*G10L 21/0216* (2013.01)

(52) U.S. Cl.
CPC .......... *H04R 25/43* (2013.01); *G10L 21/0216* (2013.01); *G10L 2021/02165* (2013.01); *H04R 2225/43* (2013.01); *H04R 2225/67* (2013.01); *H04R 2410/07* (2013.01)

(56) References Cited

U.S. PATENT DOCUMENTS

2014/0185819 A1* 7/2014 Gleissner ............. H04R 1/1083
381/71.6
2017/0078790 A1* 3/2017 Yen ..................... G10L 21/0216

OTHER PUBLICATIONS

K. Chung, Wind Noise in Hearing Aids: I. Effect of Wide Dynamic Range Compression and Modulation-Based Noise Reduction, International Journal of Audiology 2011; Early Online, 1 -13.

K. Chung, Wind noise in hearing aids: II. Effect of microphone directivity, International Journal of Audiology, 2012; 51:29-42.

K. Chung, Microphone Directionality, Pre-Emphasis Filter, and Wind Noise in Cochlear Implants, Journal of the American Academy of Audiology, 2011, 22:586-600.

E. Nel, An Industry First: Wind Noise Reduction for Cochlear Implants APSCI, 2013, Hydrobad.

K. Chung, Wind Noise in Hearing Aids With Directional and Omnidirectional Microphones: Polar Characteristics of Behind-the-Ear Hearing Aids, The Journal of the Acoustical Society of America, Apr. 2009 125, 2243-2259.

P. Dawson, Clinical Evaluation of Signal-to-Noise Ratio-Based Noise Reduction in Nucleus(R) Cochlear Implant Recipients, Ear and Hearing 2011, vol. 32, pp. 382-390.

M. Goorevich, Effect of a Wind Noise Reduction Algorithm on Cochlear Implant Sound Processing 12th International Conference on Cochlear Implants and other Implantable Technologies, 2012, Baltamore, Maryland, USA.

J. Grenner, A Comparison of Wind Noise in Four Hearing Instruments. Scandinavian Audiology 2000, 171-174, vol. 29.

A. Hersbach, Combining Directional Microphone and Single-Channel Noise Reduction Algorithms: A Clinical Evaluation in Difficult Listening Conditions With Cochlear Implant Users. Ear and Hearing e13-e23, vol. 33.

S. Mauger, Cochlear Implant Optimized Noise Reduction, Journal of Neural Engineering 2012, 9, 065007.

S. Mauger, Perceptually Optimized Gain Function for Cochlear Implant Signal-to-Noise Ratio Based Noise Reduction, The Journal of the Acoustical Society of America 2012, 327-336, vol. 131.

S. Mauger, Clinical Evaluation of the Nucleus® 6 Cochlear Implant System: Performance Improvements with SmartSound iQ, International Journal of Audiology 2014, 564-576, vol. 53.

J. Patrick, The Development of the Nucleus Freedom Cochlear Implant System, Trends Amplif 2016, 175-200, vol. 10.

A. Spriet, Speech Understanding in Background Noise With the Two-Microphone Adaptive Beamformer BEAM in the Nucleus Freedom Cochlear Implant System, Ear and Hearing 2007, 2-72, vol. 28, No. 1.

J. Wolfe, Benefit of a Commercially Available Cochlear Implant Processor With Dual-Microphone Beamforming: a Multi-Center Study. Otology & Neurotology : Official Publication of the American Otological Society, American Neurotology Society [and] European Academy of Otology and Neurotology 2012, 553-560, vol. 33.

* cited by examiner

SOUND PROCESSING IN A HEARING DEVICE USING EXTERNALLY AND INTERNALLY RECEIVED SOUNDS

CROSS REFERENCE TO RELATED APPLICATION

The present application claims priority to U.S. Provisional Application No. 62/068,048 filed on Oct. 24, 2014, which is incorporated herein by reference in its entirety.

BACKGROUND

Unless otherwise indicated herein, the description in this section is not prior art to the claims and is not admitted to be prior art by inclusion in this section.

Various types of hearing devices provide people with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

People with some forms of conductive hearing loss may benefit from hearing devices such as hearing aids or electromechanical hearing devices. A hearing aid, for instance, typically includes at least one small microphone to receive sound, an amplifier to amplify certain portions of the detected sound, and a small speaker to transmit the amplified sounds into the person's ear. An electromechanical hearing device, on the other hand, typically includes at least one small microphone to receive sound and a mechanism that delivers a mechanical force to a bone (e.g., the recipient's skull, or a middle-ear bone such as the stapes) or to a prosthesis (e.g., a prosthetic stapes implanted in the recipient's middle ear), thereby causing vibrations in cochlear fluid.

Further, people with certain forms of sensorineural hearing loss may benefit from hearing devices such as cochlear implants and/or auditory brainstem implants. Cochlear implants, for example, include at least one microphone to receive sound, a unit to convert the sound to a series of electrical stimulation signals, and an array of electrodes to deliver the stimulation signals to the implant recipient's cochlea so as to help the recipient perceive sound. Auditory brainstem implants use technology similar to cochlear implants, but instead of applying electrical stimulation to a person's cochlea, they apply electrical stimulation directly to a person's brain stem, bypassing the cochlea altogether, still helping the recipient perceive sound.

In addition, some people may benefit from hearing devices that combine one or more characteristics of the acoustic hearing aids, vibration-based hearing devices, cochlear implants, and auditory brainstem implants to perceive sound.

SUMMARY

Hearing devices such as these can be configured to be totally implantable or otherwise capable of being inserted in a recipient without requiring an external unit to function. In an example operation, an internal unit of a totally implantable hearing device may receive at one or more internal microphones (or other audio transducers) a sound from an acoustic environment. Each internal microphone may output an internal sound signal component, which the internal unit may process to provide an internal sound signal. The internal unit may further process the internally-received sound signal to generate stimulation data from which the internal unit may generate one or more stimuli. The internal unit may then deliver the one or more stimuli to a body part in an auditory pathway of the recipient (e.g., a cochlea, an auditory nerve, a region of the recipient's brain, or any other body part that contributes to the perception of sound), thereby causing the recipient to perceive at least a portion of the received sound.

The recipient can also use an external unit of the totally implantable hearing device, which the recipient can wear on her body, perhaps by magnetically coupling the external unit to the internal unit. When used, the external unit may provide a power signal to recharge a power supply of the internal unit, and the external unit may also provide external sound processing functionality. The external unit may thus receive at two or more external microphones (or other audio transducers) the sound from the acoustic environment. Each external microphone may similarly provide an external sound signal component, which the external unit may process to provide an external sound signal. The external unit may then send to the internal unit (e.g., via an inductive link) the external sound signal. The internal unit might thus have the option of generating the stimulation data based on the externally-received sound signal and/or the internally-received sound signal.

Generally speaking, the internal unit would utilize the external unit as a primary sound source, as the presence of skin and/or other tissue between the internal unit and the acoustic environment could reduce the quality of sounds received at the internal unit, as compared to the quality of sounds received at the external unit. Thus, generating stimulation data based on externally-received sounds may generally provide the recipient with an advantageous representation of the environmental sound. Under certain conditions, however, the quality of some parts of sounds received at the internal unit may be better than the quality of corresponding parts of sounds received at the external unit. These conditions are referred to herein as "triggering conditions." One possible triggering condition is the presence of a non-correlative sound in the external sound signal. As used herein, a non-correlative sound refers to a sound resulting in random, and sometimes large, differences in the amount of energy in low-frequency components of sound received at any two the external unit's audio transducers. Other triggering conditions are also possible.

Two non-exclusive examples of non-correlative sounds are an incoherent-source sound and a near-field sound. As used herein, an incoherent-source refers to random fluctuations in the air pressure (e.g., eddies) around the diaphragm(s) of one or more microphones, thereby inducing noise in the system. Each external signal component would thus include varying amounts of noise, typically (but not exclusively) at low frequencies. When the external unit processes the external sound signal components from two microphones, perhaps to make a directional microphone, the resulting external sound signal would likely have a greater amount of low-frequency noise than would be present in any one external sound signal component. A common example of an incoherent-source sound is wind noise, though other examples are possible as well.

A near-field sound, as that term is used herein, generally refers to sounds originating within a distance of approximately twenty centimeters of the external microphones. In some situations, for instance, wind noise received at certain angles can be a near-field sound. Other example sources of a near-field sound may include a person talking to the recipient in close proximity to the external microphones (e.g., when the speaker wants to whisper to the recipient) or a sound source that the recipient places within close proximity to the external microphones, such as a telephone. If the external unit amplifies low-frequency components of a near-field sound, the resulting amplification of the low-frequency components of the near-field sound may result in the externally-received sound signal having significantly increased gains in the lower frequencies as compared to a sound received at an internal microphone, perhaps on the order of approximately forty (or more) decibels (many hearing devices do this to account for an octave roll-off for far-field sounds (e.g., sounds originating from sources beyond twenty centimeters) at low frequencies).

Generating stimulation data based on such a processed sound signal (e.g., a sound signal processed from a sound that includes an incoherent-source sound or a near-field sound) could result in high-amplitude stimuli corresponding to low frequencies, which could impede the recipient's ability to perceive mid- or high-frequency sounds. Amplifying wind noise, for instance, could mask low-frequency sounds in the acoustic environment, thereby impeding the recipient's ability to perceive low-frequency sounds in the environment as well. Moreover, when a near-field sound is received, the internal unit may generate a disproportionate number of high-intensity stimuli at low frequencies, which could result in altogether omitting sounds in middle frequencies and/or high frequencies from the stimulation data.

The present disclosure provides an improved method, and a corresponding systems and devices, usable by a sound processor of a totally implantable hearing device to process sounds. The sound processor—which could be a component of the internal unit and/or the external unit—may determine whether a triggering condition is present in an externally-received sound. If the triggering condition is present, the sound processor may use at least a portion of the internally-received sound to generate the processed sound signal from which the processing component will generate stimulation data.

As one example, when a triggering condition is present in the externally-received sound, the sound processor may generate the processed sound by mixing the internal sound signal with the externally-received sound. A percentage of each sound signal may depend in part on the severity of the triggering condition. The percentage of the internally-received sound may vary directly with the severity of the triggering condition, whereas the percentage of the externally-received sound may vary inversely with the severity of the triggering condition.

As another example, individual frequency bands or ranges, which may be implemented as frequency bands (or ranges) or as Fast Fourier Transform (FFT) bins, may be evaluated for a triggering condition. In this example, the sound processor may generate the processed sound by mixing the externally-received sound with the internally-received sound in each frequency band or FFT bin in which a triggering condition is present in the externally-received sound. The percentage of the internally-received sound may vary directly with the severity of the triggering condition, whereas the percentage of the externally-received sound may vary inversely with the severity of the triggering condition.

As another example, the sound processor could generate the processed sound signal such that the processed sound signal includes (a) one or more spectral components of the internally-received sound signal and (b) one or more spectral components of the externally-received sound signal, with each spectral component corresponding to an energy level of a respective sound signal at a given frequency (or frequency band). For instance, if the triggering condition affects low-frequency spectral components of the externally-received sound, the processed sound signal may include one or more spectral components of the internal sound signal that are below a cutoff frequency. The processed sound could also include one or more spectral components of the external sound signal that are above the cutoff frequency. A value of the cutoff frequency may depend in part on the severity of the triggering-condition—the more frequency bands of the external unit the triggering condition affects, the higher the cutoff frequency.

Accordingly, in one aspect, a method is disclosed. The method includes receiving an external sound signal transduced externally to a recipient from an ambient sound and an internal sound signal transduced internally to the recipient from the ambient sound. The method also includes determining that a triggering condition is present in the external sound signal. In response to determining that the triggering condition is so present, the method further includes (i) generating a processed sound signal that includes spectral information from at least a portion of the internal sound signal, (ii) generating a stimulation signal that is based on the processed sound signal, and (iii) stimulating the recipient with the stimulation signal. Stimulating the recipient with the stimulation signal may cause the recipient to perceive at least a portion of a sound.

In another respect, a system is disclosed. The system includes one or more external microphones positioned externally to a body of a recipient, one or more internal microphones implanted in the body of the recipient, and at least one processing component. The at least one processing component is configured to receive a set of external sound signal components from the one or more external microphones and a set of internal sound signal components from the one or more internal microphones. The at least one processing component is also configured to process (a) the first set of sound signals to provide an external sound signal and (b) the second set of sound signals to provide an internal sound signal. Additionally, the at least one processing component is configured to identify a non-correlative sound in the external sound signal. In response to identifying the non-correlative sound in the external sound signal, the at least one processing component is further configured to (1) determine an amount of spectral information of the external sound signal to include in a processed sound signal, (2) determine an amount of spectral information of the internal sound signal to include in the processed sound signal, and (3) generate the processed sound signal according to the determined amounts of spectral information.

In yet another aspect, a device configured to be implanted in a recipient is disclosed. The device comprises at least one audio transducer, a stimulation component configured to stimulate a body part of the recipient to cause the recepient to perceive at least a portion of a sound, and at least one sound processor. The at least one processor is configured for processing a sound signal component received from the at least one audio transducer to provide an internal sound signal. The internal sound signal includes spectral information indicative of an ambient sound as received at the at least one audio transducer through while implanted in the recipient. The at least one processor is also configured for receiving from a device external to the recipient an external signal that includes information indicative of the ambient sound as received at the device external to the recipient. Further, the at least one processor is configured for determining that the external signal includes information indicative that the ambient sound, as received at the device external to the recipient, includes a non-correlative sound. And in response to determining that the external signal includes information indicative of the non-correlative sound, the at least one processor is additionally configured for (a) generating a stimulation signal based at least in part on spectral information included in the internal sound signal, and (b) causing the stimulation component to stimulate the body part based on the stimulation signal.

In still another respect, another device is disclosed. The device comprises a first audio transducer and a second audio transducer and a sound processing component. The sound processing component is configured to receive a first external sound signal component from the first audio transducer and a second external sound signal component from the second audio transducer. The sound processing component is further configured to process the first external sound signal component and the second external sound signal component to provide an external sound signal. Additionally, the sound processing component is configured to identify in the external sound signal an indication of a non-correlative sound. In response to identifying the non-correlative sound, the sound processing component is further configured to send to an implanted unit of a hearing device an external signal that includes an indication of the external sound signal including the non-correlative sound.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

DETAILED DESCRIPTION

Figure 1:
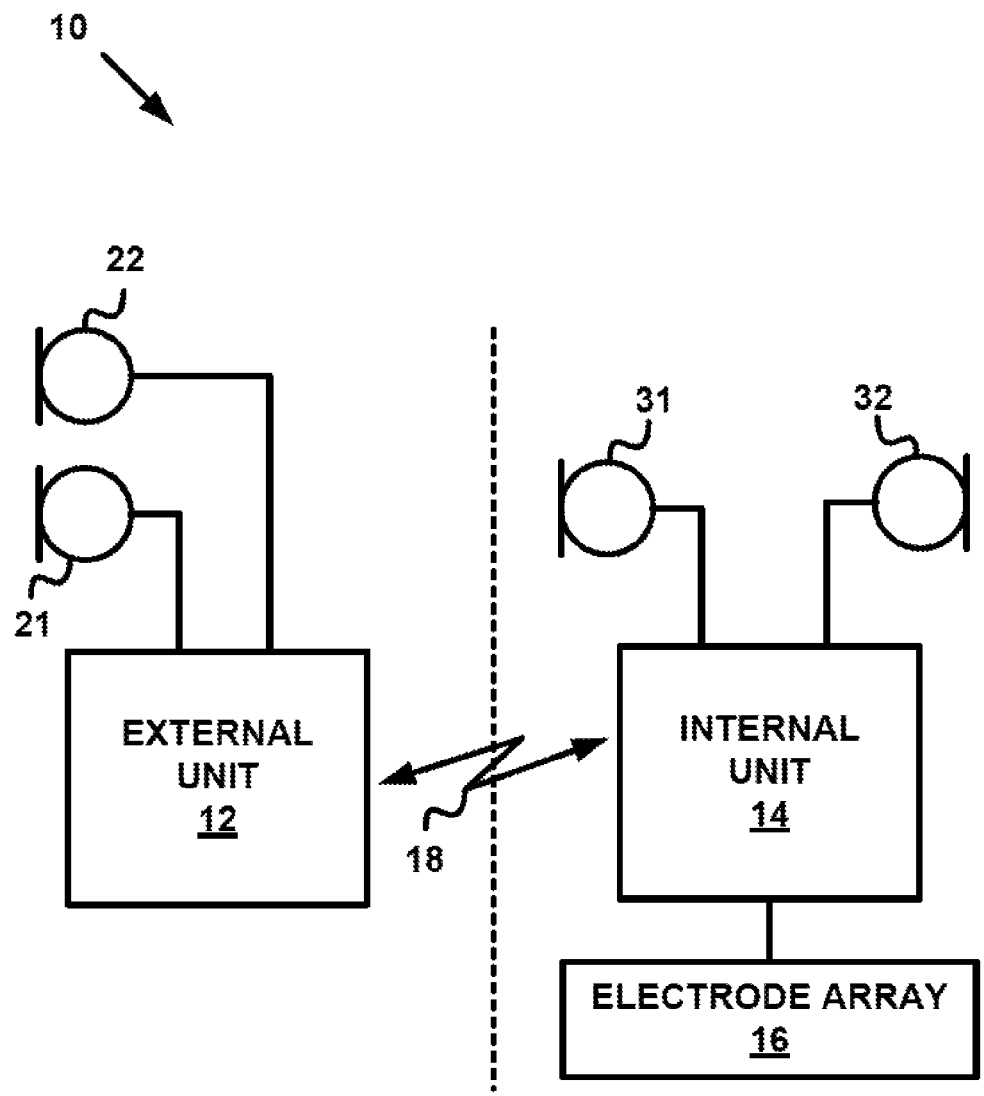
FIG. 1 is a simplified block diagram of an example system in which features of the present disclosure can be implemented.

Referring to the drawings, as noted above, FIG. 1 is a simplified illustration of a system in which features of the present disclosure can be implemented. In particular, FIG. 1 depicts a hearing device 10 that includes an external unit 12 and an internal unit 14. By way of example, the hearing device 10 is depicted as a cochlear implant. In this case, the internal unit 14 includes an electrode array 16 configured to stimulate one of the recipient's cochleae. Specifically, the electrode array 16 may include a plurality of electrodes, each of which corresponds to a frequency band. The internal unit 14 may cause one or more of the electrodes to deliver an electrical stimulus to a region of the cochlea, thereby causing the recipient to perceive sound at a particular frequency. In other examples, however, the hearing device 10 may be a different type of hearing device. For instance, if the hearing device 10 is an auditory brainstem implant, the electrode array 16 may be adapted to be inserted into a portion of the recipient's brain. Or in examples in which the hearing device 10 does not deliver electrical stimuli to the recipient, a different stimulation component would replace the electrode array 16. Further, the internal unit 14 may not necessarily be implanted in the recipient's body in each embodiment of the hearing device 10. For example, the recipient might insert the internal unit 14 into one of the recipient's ear canals when the recipient uses the hearing device 10.

As shown in FIG. 1, the external unit 12 and the internal unit 14 each include two audio transducers: the external unit 12 includes a first external microphone 21 and a second external microphone 22, and the internal unit 14 includes a first internal microphone 31 and a second internal microphone 32, with each of the internal microphones 31, 32 being implanted or otherwise placed inside the recipient's body (e.g., placed in the recipient's ear canal). In other examples, however, each of the external microphones 21 and 22 and the internal microphones 31 and 32 may be a different microphone, if not a different audio transducer.

In an example implementation, the external unit 12 receives an ambient sound at each of a first external microphone 21 and a second external microphone 22. The external unit 12 may then process an external sound signal component received from each external microphone 21, 22 to generate an external sound signal, perhaps by using delayed and subtracted signals, such as used in directional microphone technologies. The external sound signal may be processed so as to include one or more spectral components.

The external unit 12 may send to the internal unit 14 the processed external sound signal (or perhaps the received external sound signal components) to the internal unit via a link 18. The link 18 is preferably a wireless induction link in order to facilitate transmission of data between the external unit 12 and the internal unit 14 as well as a power signal from external unit 12 to the internal unit 14. In other examples, however, the link 18 may be a different wireless link, perhaps one that conforms to an industry-recognizes wireless protocol, or even a wired link. If the internal unit 14 receives the external sound signal components, the internal unit 14 may process the external sound signal components to generate the external sound signal.

The internal unit 14 may thus receive the external sound signal. The internal unit 14 may also receive an internal sound signal component from each of the first internal microphone 31 and the second internal microphone 32, which the internal unit 14 may process to generate an internal sound signal. In line with the above discussion, the internal unit 14 may generate from one or both of the internal sound signal or the external sound signal a processed sound signal. Based on the processed sound signal, the internal unit 14 may generate stimulation data that can then be used to generate one or more stimuli. To determine which, or how much, of the external sound signal and/or the internal sound signal to include in the processed sound signal, the internal unit 14 may first determine whether a triggering condition is present.

As previously discussed, the triggering condition generally refers to a condition in the acoustic environment that has a more adverse effect on the quality of an externally-received sound (e.g., a sound received at the first external microphone 21 and/or the second external microphone 22) than the quality of an internally-received sound (e.g., a sound received at the first internal microphone 31 and/or the second internal microphone 32). The internal unit 14 may analyze the spectral components of the external sound signal, or perhaps the spectral components of the external spectral components if received from the external unit 12, in order to determine whether a triggering condition is present in the external sound signal. As one possible example, if the triggering condition is wind noise (i.e., an incoherent-source sound and/or a near-field sound), the internal unit 14 may employ a suitable analysis of the external sound signal for detecting wind noise in an audio signal. If the internal unit 14 determines that a triggering condition is not present in the external sound signal, the internal unit 14 may generate the stimulation data based on the external sound signal. On the other hand, if the internal unit 14 determines that a triggering condition is present in the external sound signal, the internal unit 14 may include at least a portion of the internal sound signal in the processed sound signal.

In one example, the internal unit 14 may mix the external sound signal and the internal sound signal in response to determining that a triggering condition is present in the external sound signal. To determine a respective percentage of each of sound signal to include in the processed sound signal, the internal unit 14 may determine a correlation factor of the external sound signal. The correlation factor may represent a correlation between a first external sound signal component and a second external sound signal component. A correlation factor of one would indicate that the first external sound signal component is identical to the second external sound signal component, whereas a correlation factor of zero would indicate a complete mismatch between the first external sound signal component and the second external sound signal component.

Figure 2A:
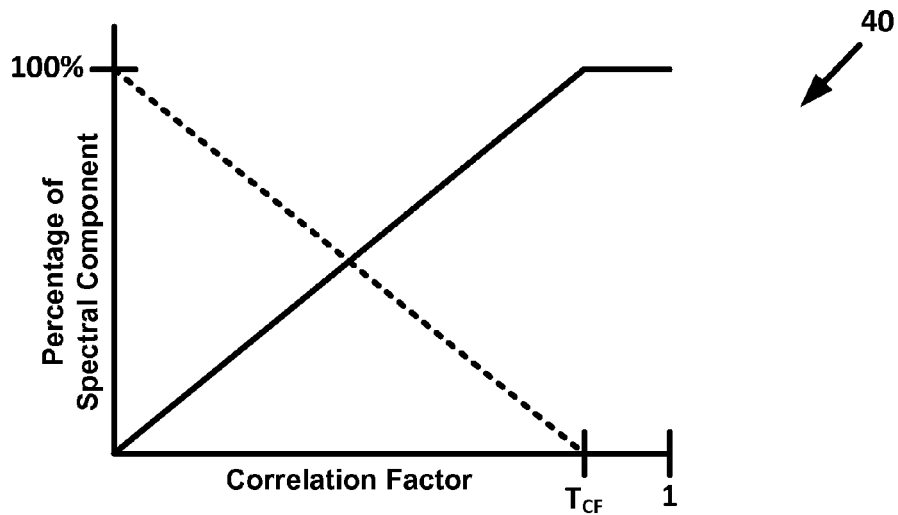
FIG. 2A is an example graph of a correlation factor of an external sound signal versus percentages of the external sound signal and an internal sound signal used to mix the external sound signal and the internal sound signal.

FIG. 2A illustrates a graph 40 of the correlation factor of the external sound signal versus respective percentages of the external sound signal and the internal sound signal that are included in the processed sound signal.

Based on the graph 40, the internal unit 14 would include in the processed sound signal 100% of the external sound signal when the correlation factor is greater than or equal to a threshold correlation factor ($CF_t$ in FIG. 2A). The threshold correlation factor may correspond to a correlation factor for the external sound signal at which a triggering condition is not, or is not likely to be, present in the external sound signal. When the threshold correlation factor is below the threshold correlation factor—which may indicate that a triggering condition is present in the external sound signal—the internal unit 14 may include a percentage of the internal sound signal in the processed sound signal. As the severity of the triggering condition increases, the correlation factor may decrease, and the internal unit 14 may consequently include in the processed sound signal a larger portion of the internal sound signal and a smaller portion of the external sound signal.

The threshold correlation factor may vary for each frequency band. Alternatively, each frequency band could have the same threshold correlation factor. Similarly, the respective percentages of the internal sound signal and the external sound signal included in one frequency band of the processed sound signal may vary from the respective percentages of the internal sound signal and the external sound signal included in another frequency band of the processed sound signal. Alternatively, the respective percentages of the internal sound signal and the external sound signal may be the same for each frequency band, in which case the presence of a triggering condition may be based on a broadband correlation factor. Moreover, while the respective percentages of the external sound signal and the internal sound signal are shown as varying linearly between zero and the threshold correlation factor, the respective percentages could instead vary nonlinearly, for example, logarithmically or exponentially.

Figure 2B:
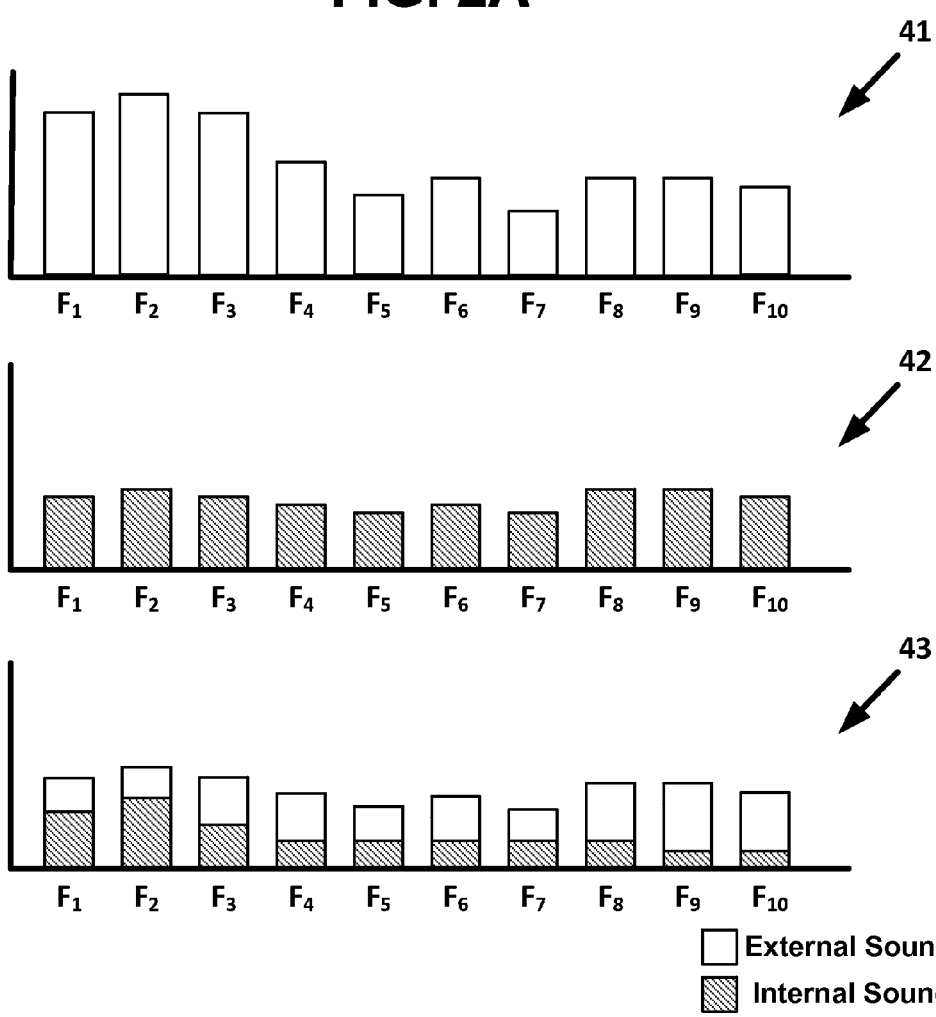
FIG. 2B shows example spectra of an external sound signal, an internal sound signal, and a processed sound signal.

To further illustrate the spectral composition of the processed sound signal, FIG. 2B shows example spectra of several sound signals. Specifically, FIG. 2B illustrates a first spectrum 41 of an example external sound signal, a second spectrum 42 of an example internal sound signal, and a third spectrum 43 of an example processed sound signal. While each spectrum in FIG. 2B and other figures herein shows ten frequency bands, it is understood that the internal unit 14 may use fewer than ten frequency bands or up to twenty-two or more frequency bands.

To generate the processed sound signal shown in the third spectrum 43, the internal unit 14 may have determined a correlation factor for each frequency band, and based on a graph for each frequency like the graph 40, and the internal unit 14 may have determined percentages of the external sound signal and the internal sound signal to include in each frequency band. Thus, in the example depicted in FIG. 2B, the respective percentages of the internal sound signal and the external sound signal included in a given frequency band varies from frequency band to frequency band.

In an alternative implementation, the internal unit 14 could have used fixed percentages of the external sound signal and the internal sound signal to apply when determining the spectral composition of each frequency band. For instance, if the internal unit 14 determined that the processed sound signal should include sixty percent of the internal sound signal and forty percent of the external sound signal, then each frequency band would include sixty percent of the internal sound signal at that frequency band and forty percent of the external sound signal at the frequency band.

Figure 3:
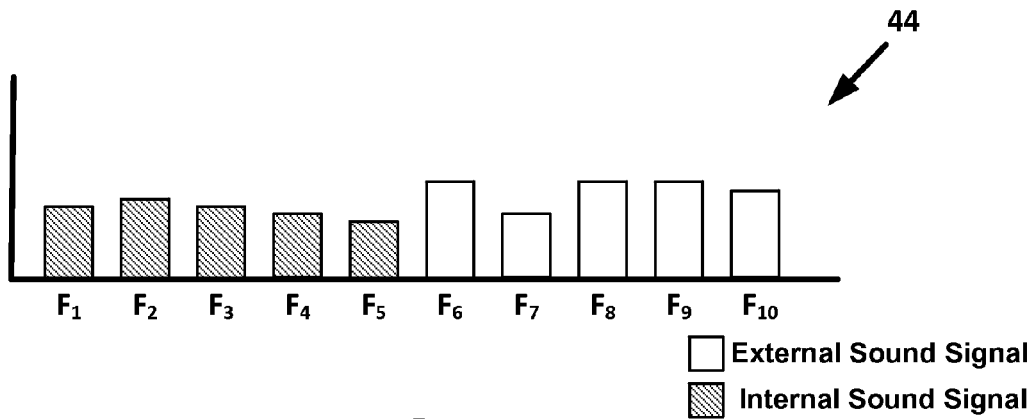
FIGS. 3, 4A, and 4B shows example spectra of processed sound signals.

In another example, the internal unit 14 may include in the processed sound signal spectral components from each of the external sound signal and the internal sound signal when a triggering condition is present in the external sound signal. This example is illustrated in FIG. 3, which depicts a fourth example spectrum 44 of a processed sound signal. In this example, the cutoff frequency corresponds to the sixth frequency band. The internal unit 14 may have determined the cutoff frequency based on the severity of the triggering condition, or the cutoff frequency could have a fixed value determined by an audiologist (or other clinical specialist) during a fitting procedure. In the fourth spectrum 44 then, the processed sound signal includes the spectral components of the internal sound signal in each of the first five frequency bands ($F_1$-$F_5$) and the spectral components of the external sound signal in the last five frequency bands ($F_6$-$F_{10}$).

In other examples, the internal unit 14 may include in the processed sound signal more or fewer spectral components of the internal sound signal. For instance, the internal unit 14 may identify each frequency band in which a triggering condition is present in the external sound signal. For each identified frequency band, the spectral component of the processed sound signal is the spectral component of the internal sound signal at that frequency band. And for the remaining frequency bands, the spectral component of the processed sound signal is the spectral component of the external sound signal at that frequency band.

As yet another example, the internal unit 14 may include in the processed sound signal the spectral components of the external sound signal in a first set of frequency bands, the spectral components of the internal sound signal in a second set of frequency bands, and a mix of the external sound signal and the internal sound signal in a third set of frequency bands. Such examples are illustrated in FIGS. 4A and 4B.

Figure 4A:
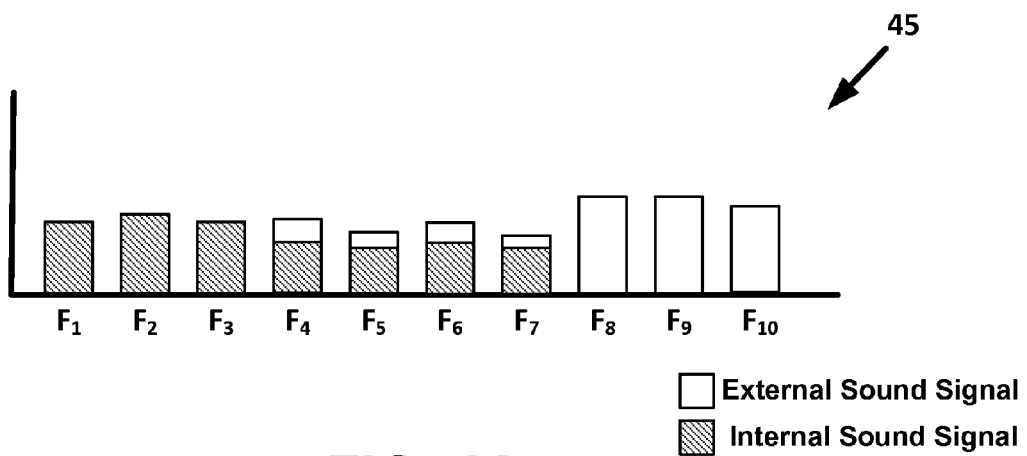

FIG. 4A shows a fifth example spectrum 45 of a processed sound signal. In the fifth spectrum 45, the processed sound signal includes the spectral components of the internal sound signal in the first three frequency bands ($F_1$-$F_3$) and the spectral components of the external sound signal in the last three frequency bands ($F_8$-$F_{10}$). In the middle four frequency bands ($F_4$-$F_7$), the external sound signal and the internal sound signal are mixed. As with the previous example, the number of frequency bands that are mixed or the number of spectral components from a specific sound signal could vary based on the severity of the triggering condition.

Figure 4B:
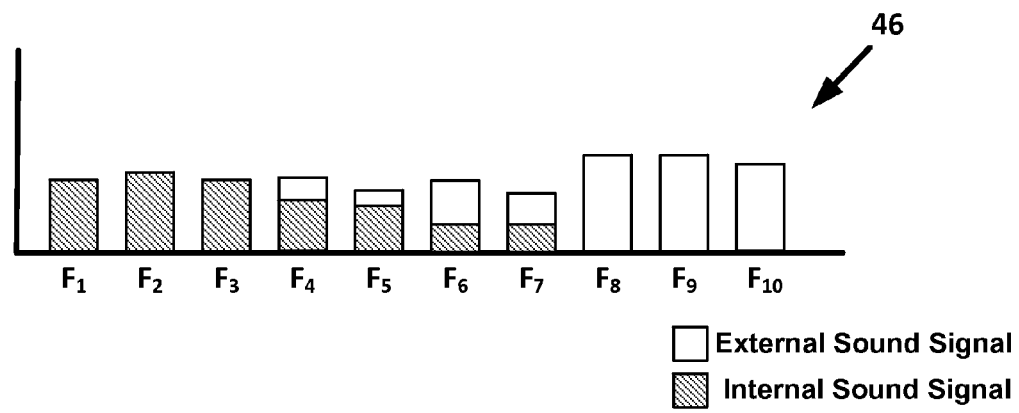

FIG. 4B shows a sixth example spectrum 46 of a processed sound signal. Like the fifth spectrum 45, the sixth spectrum 46 shows the processed sound signal as including the spectral components of the internal sound signal in the first three frequency bands ($F_1$-$F_3$) and the spectral components of the external sound signal in the last three frequency bands ($F_8$-$F_{10}$). In the four middle frequency bands ($F_4$-$F_7$), the external sound signal and the internal sound signal are mixed. Whereas each of the middle four frequency bands in the fifth spectrum 45 have the same spectral composition (i.e., the percentage of the internal sound signal and the percentage of the external sound signal are the same for each frequency band), the respective percentages of the internal sound signal and the external sound signal vary among the four middle frequency bands in the sixth spectrum 45.

In the preceding examples, the internal unit 14 is described as determining whether a triggering condition is present in the external sound signal. Alternatively, the external unit 12 could make such a determination when generating the external sound signal and could determine how much of the internal sound signal to include in the processed sound signal. For example, upon determining that a triggering condition is present in the external sound signal, the external unit 12 may send to the internal unit 14 via the wireless link 18 a status signal indicative of a triggering condition. The external unit 12 may also identify in the status signal one or more frequency bands in which the triggering condition is present. The external unit 12 may then send the status signal and the external sound signal simultaneously, perhaps by combining the status signal and the external sound signal into one signal. Or the external unit 12 may send the status signal and external sound signal in separate transmissions.

In some acoustic environments, the recipient may want to force the internal unit 14 to generate the processed sound signal using at least a portion of the internal sound signal regardless of whether a triggering condition is present in the external sound signal. For example, the recipient may determine that she perceives sounds better in certain acoustic environments when at least a portion of the internal sound signal is used to generate the processed sound signal. In this case, the recipient may interact with the external unit 12, perhaps via a user-input component of a user-interface module, to force the internal unit 14 to use at least a portion of the internal sound signal when generating the processed sound signal. The recipient could also interact with the external unit 12 to select respective percentages of the sound signals to use when generating the processed sound signal and/or a value of the cutoff frequency. Alternatively, the respective percentages of the sound signals and/or the value of the cutoff frequency may be fixed by an audiologist or at the point of manufacture of the hearing device 10.

Moreover, while the preceding examples describe the triggering conditions occurring primarily in lower frequency bands, it should be noted that a triggering condition could also be present in middle frequency bands and/or higher frequency bands. For example, a near-field sound having a high fundamental frequency may result in noise in a corresponding frequency band of the external sound signal similar to the noise caused by non-correlative sounds.

The internal unit 14 may implement any one, or perhaps more than one, of the above-described processing techniques in a number of ways. As one example, the internal unit 14, upon detecting a triggering condition in the external sound signal, may immediately (e.g., within about 1 millisecond) begin including a portion of the internal sound signal in the processed sound signal. Similarly, the internal unit 14, upon determining that the triggering condition is no longer present in the external sound signal, may immediately (e.g., within about 1 millisecond) stop including a portion of the internal sound signal in the processed sound signal.

As another example, the internal unit 14 could include a portion of the internal sound signal in the processed sound signal when the internal unit 14 determines that a triggering condition is present in the external sound signal for the duration of a first time period. The first time period could be anywhere from about 10 milliseconds to as long as 100 milliseconds, or perhaps even as long as 10 seconds. The internal unit 14 could also continue including a portion of the internal sound signal in the processed sound signal until determining that a triggering condition has not been present in the external sound signal for the duration of a second time period. The second time period could be longer, shorter, or the same as the first time period.

As a variation on the previous example, the internal unit 14 could immediately begin including a portion of the internal sound signal in the processed sound signal upon determining that a triggering condition is present, but then wait until determining that a triggering condition has not been present in the external sound signal for the second time period before the internal unit 14 stops including a portion of internal sound signal in the processed sound signal. Or the internal unit 14 could wait until a triggering condition has been present in the external sound signal for at least the first time period before including a portion of the internal sound signal in the processed sound signal, and could immediately stop including a portion of the internal sound signal in the processed sound signal as soon as the internal unit 14 determines that a triggering condition is not present in the external sound signal.

As yet another example, the internal unit 14 could gradually increase and/or decrease the mixing ratio and/or the number of frequency channels included in the processed sound signal. For instance, if the internal unit 14 determines that a mixing ratio is about 50% of the internal sound signal and the external sound signal, the internal unit 14 may gradually increase the percentage of the internal sound signal included in the processed sound signal from 0% to 50% over a time interval. Additionally or alternatively, the internal unit 14, upon determining that a triggering condition is not present in the external sound signal, could gradually reduce the percentage of the internal sound signal included in the processed sound signal over a timer interval from 50% to 0%, for example. Like the time periods described in the previous example, a given time interval could be as short as about 10 milliseconds or as long 100 milliseconds, or even as long as 10 seconds.

In the preceding examples, the internal unit 14 determines when to switch to including at least a portion of the internal sound signal in the processed sound signal. In some implementations, however, the external unit 12 could make this determination and include data indicative of the determination in a signal transmitted to the internal unit 14.

Figure 5:
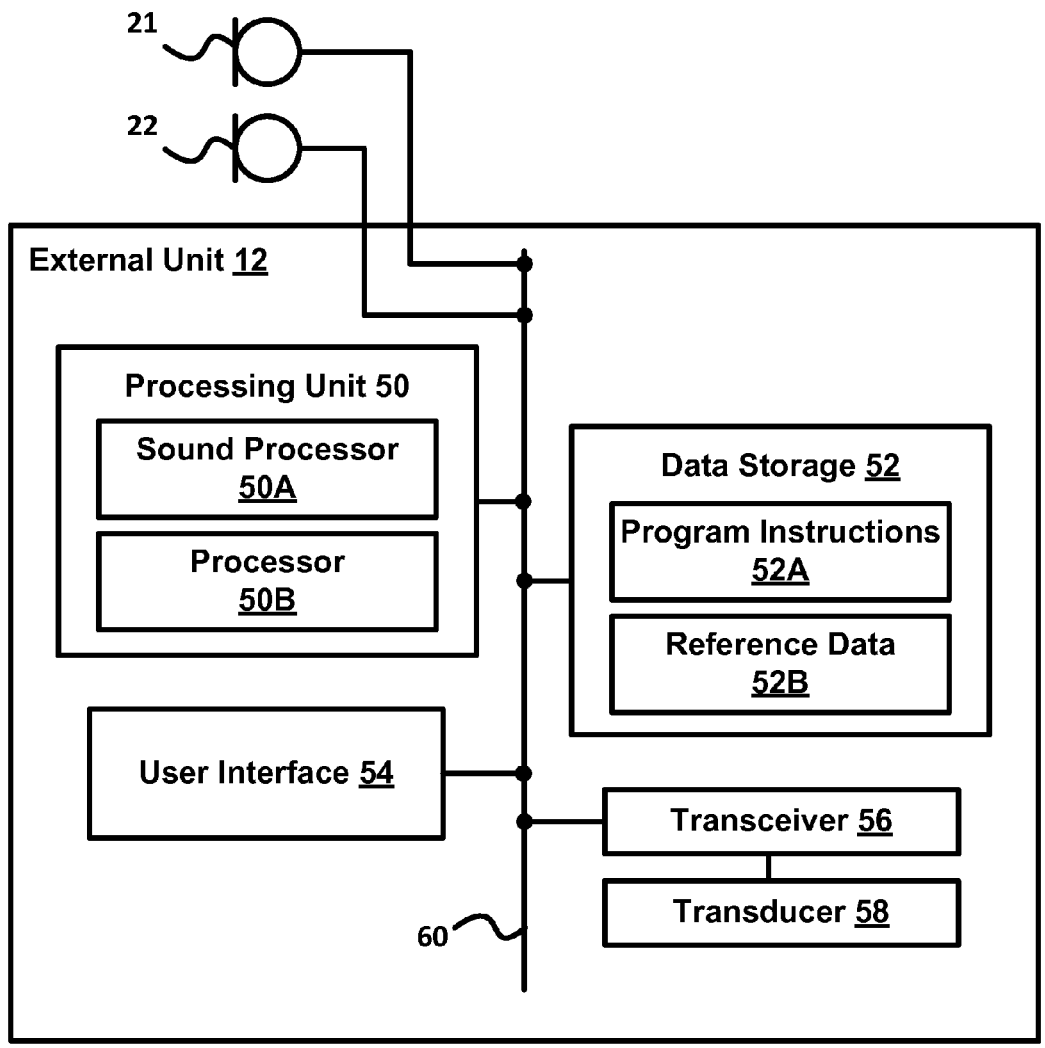
FIG. 5 is a simplified block diagram depicting components of an example external unit of a hearing device.

Turning now to FIG. 5, the external unit 12 includes the first external microphone 21, the second external microphone 22, a processing unit 50, data storage 52, a user interface 54, and a transceiver 56, which are communicatively linked together by a system bus, network, or other connection mechanism 60. The external unit 12 also includes a transducer 58, such as an inductive coil, that is electrically connected to the transceiver 56 to facilitate communications with the internal unit 14 via the link 18 and transferring power from the external unit 12 to the implanted unit 14.

In an example arrangement, these components are included in a single housing. In alternative arrangements, the components could be provided in or more physical units for use by the recipient. For example, the external microphones 21 and 22, the processing unit 50, the data storage 52, the user-interface module 54, and the transceiver 56 may be included in a behind-the-ear housing, while the transducer 58, and perhaps a magnet, may be included in a separate housing that is connected to the behind-the-ear housing by a cable. Other arrangements are possible as well.

In the arrangement as shown, each of the external microphones 21 and 22 may be arranged to receive audio input, such as audio coming from an acoustic environment, and to provide a corresponding external sound signal component (e.g., electrical or optical, possibly sampled) to the processing unit 50. For instance, the external microphones 21 and 22 may be positioned on an exposed surface of the housing of the external unit 12. Further, the microphones 21 and 22 may comprise additional and/or other audio transducers, each of which could also be positioned on an exposed surface of the housing of the external unit 12.

The processing unit 50 may then comprise one or more digital signal processors (e.g., application-specific integrated circuits, programmable logic devices, etc.), as well as analog-to-digital converters. As shown, at least one such processor functions as a sound processor 50A acts to generate the external sound signal by processing the external sound signal components. The sound processor 50A may also be configured to determine whether a triggering condition is present in the external sound signal, and perhaps to identify one or more frequency bands in which the triggering condition is present. If a triggering condition is not present in the external sound signal, the sound processor 50A may be additionally configured to generate stimulation data. Further, another such processor 50B could be configured to receive and process inputs received via the one or more user-input components of the user-interface module 54 and to provide outputs via the one or more display components of the user-interface module 54. Alternatively, all processing functions, including functions for implementing the user interfaces, could be carried out by the sound processor 50A itself.

The data storage 52 may then comprise one or more volatile and/or non-volatile storage components, such as magnetic, optical, or flash storage, and may be integrated in whole or in part with processing unit 50. As shown, the data storage 52 may hold program instructions 52A executable by the processing unit 50 to carry out various hearing device functions described herein, as well as reference data 52B that the processing unit 50 may reference as a basis to carry out various such functions.

By way of example, the program instructions 52A may be executable by the processing unit 50 to facilitate generating the external sound signal and determining whether a triggering condition is present in the external sound signal. For instance, the instructions may cause the processing unit to combine the external sound signal components, either by adding the signals together or by subtracting one from the other. Additionally, the instructions may cause the processing unit 50 to generate a signal that causes the internal unit 14 to use at least a portion of the internal sound signal when generating the processed sound signal regardless of whether a triggering condition is present in the external sound signal.

The reference data 52B may include settings of sound-processing parameters, such as a current volume setting, a current sound-processing strategy (e.g., a strategy for combining one or more audio signals and/or selecting frequency bands at which to generate stimuli), and an active stimulation profile (e.g., a recipient-specific set of parameters used to determine an electrical stimulus based on an energy of a spectral component at each of one or more frequencies). Moreover, the reference data 52B may include information for determining respective percentages of the external sound signal and the internal sound signal on which to base the processed sound signal. Additionally or alternatively, the reference data 52B may include data for selecting one or more frequency bands of the internal sound signal to include in the processed sound signal and/or a value of a cutoff frequency below which the processed sound signal includes spectral components of the internal sound signal.

The user-interface module 54 may include one or more user-input components configured to receive an input from the recipient, or perhaps another user, that is indicative of the recipient intending for the internal unit to include at least a portion of the internal sound signal in the processed sound signal, regardless of whether the processing unit 50 detects a triggering condition in the external sound signal. The one or more user-input components may include one or more switches, buttons, capacitive-touch devices, and/or touchscreens. The user-interface module 54 may also include one or more output components, such as one or more light emitting diode (LED) arrays or displays, liquid crystal displays, and/or touchscreens. The display output may provide a visual indication of whether the user has forced the internal unit 14 to include at least a portion of the internal sound signal in the processed sound signal. Other example displays are also possible.

Figure 6:
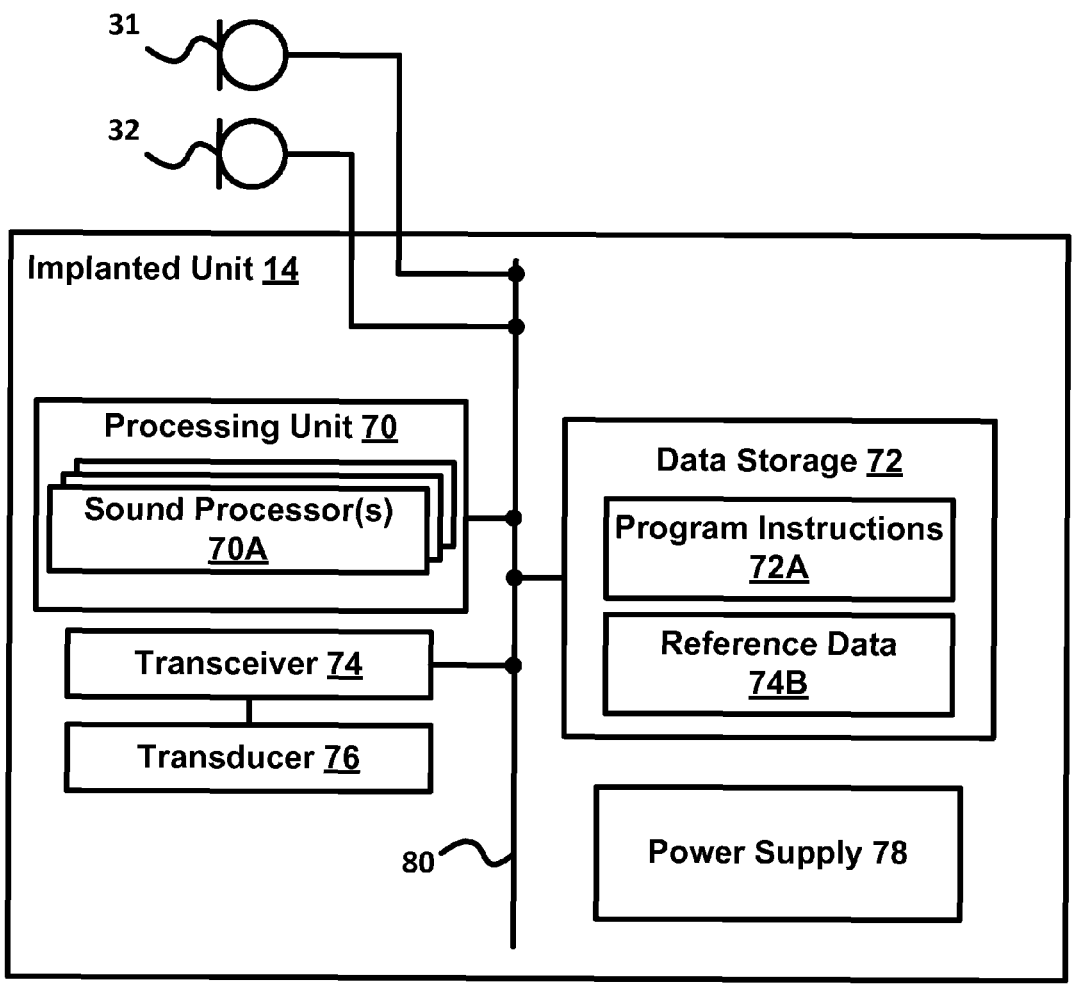
FIG. 6 is a simplified block diagram depicting components of an example internal unit of a hearing device.

Turning now to FIG. 6, the internal unit 14 includes the first internal microphone 31, the second internal microphone 32, a processing unit 70, data storage 72, and a transceiver 74, which are communicatively linked together by a system bus, network, or other connection mechanism 80. The internal unit 14 also includes a transducer 76, such as an inductive coil, that is electrically connected to the transceiver 74 to facilitate communications with the external unit 12 via the link 18. The internal unit 14 may further include a power supply 78, such as a rechargeable battery, that is configured to provide power to the components of the internal unit 14 when power is not supplied by the external unit 12 (or another processing unit coupled to the internal unit 14) via the link 18.

In an example arrangement, each of these components, with the possible exception of the internal microphones 31 and 32, are included in a single housing implanted in the recipient. Alternatively, the power supply 78 may be included in a separate implantable housing to facilitate replacement. Other arrangements are possible as well.

In practice, the first internal microphone 31 is positioned so as to receive an ambient sound, such as at a location near the recipient's skin. The first internal sound signal component may thus include the ambient sound, as received at the first internal microphone. Because it is inside the recipient, however, the first internal microphone 31 may also receive internal sounds (e.g., sounds from the recipient's organs). The second internal microphone 32 may thus positioned so as to receive the internal sounds, which are included in the second internal sound signal.

The processing unit 70 may be the same as or substantially similar to the processing unit 50 described with respect to FIG. 4. As shown, a sound processor 70A may generate the internal sound signal by processing the first internal sound signal and the second internal sound signal (which are received from the first internal microphone 30 and the second internal microphone 32, respectively). In processing such sounds, the sound processor 70A may be configured to remove internal sounds (e.g., sounds from the recipient's organs) prior to generating the processed sound signal. Using the second internal signal component as a reference, the sound processor 70A may remove the internal sounds from the first internal sound signal component, thereby producing an internal sound signal.

The sound processor 70A may also be configured to generate the external sound signal in response to receiving external sound signal components and to determine whether a triggering condition is present in the external sound signal received from the external unit 12. When the triggering condition is present in the external sound signal, or when a status signal is received from the external unit 14, the sound processor 70A may be configured to include at least a portion of the internal sound signal in the processed sound signal. Additionally, the sound processor 70A may generate stimulation data based on the processed sound signal, and the sound processor 70A may use the stimulation data to generate one or more stimuli. The sound processor 70A may then cause the electrode array 16 to deliver the one or more stimuli to a body part in the recipient's auditory pathway.

Like the data storage 52, the data storage 72 may comprise one or more volatile and/or non-volatile storage components, such as magnetic, optical, or flash storage, and may be integrated in whole or in part with processing unit 70. As shown, the data storage 72 may hold program instructions 72A executable by the processing unit 70 to carry out various hearing device functions described herein, as well as reference data 72B that the processing unit 70 may reference as a basis to carry out various such functions.

By way of example, the program instructions 72A may be executable by the processing unit 70 to facilitate determining whether a triggering condition is present in the external sound signal, and/or for determining whether a status signal was received that indicates that a triggering condition is present in the external sound signal. The program instructions 72A may also include instructions for mixing the external sound signal with the internal sound signal and/or for determining which respective spectral components of the external sound signal and the second sound to include in the processed sound signal. The program instructions 72A may also include instructions for selecting one or more frequency bands at which to stimulate the recipient, as well as program instructions for generating a sending one or more stimuli to the electrode array 16 for delivery to the recipient.

The reference data 72B may include the same or substantially similar data as the reference data 52B described with respect to FIG. 4. Additionally, the reference data 72B may include information for generating the stimulation data and/or the one or more stimuli based on the stimulation data.

Figure 7:
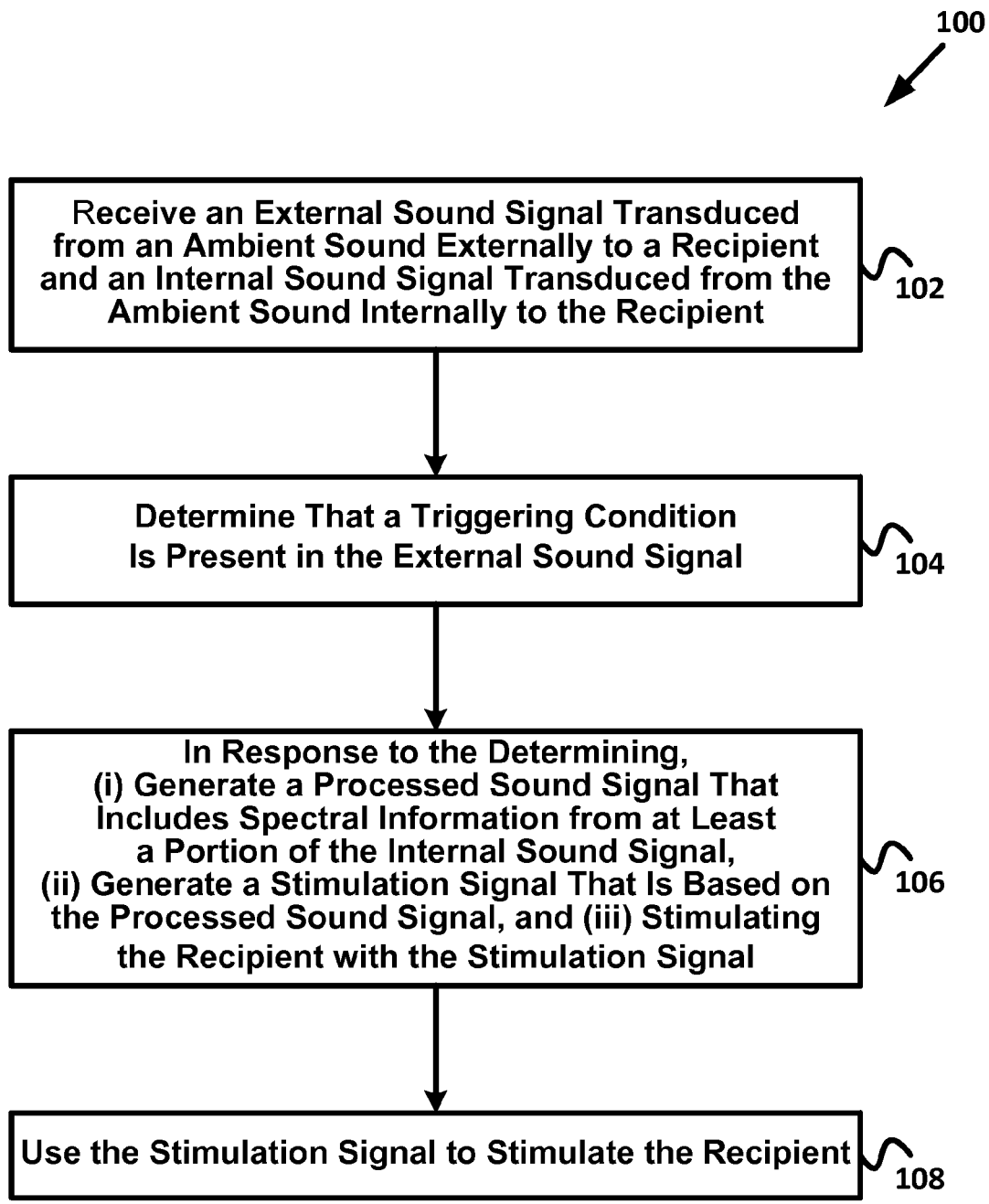
FIG. 7 is a flow chart depicting functions that can be carried out in accordance with the present disclosure.

Finally, a flow chart is shown in FIG. 7 to illustrate functions of a method 100 that can be carried out by a sound processor of an internal unit of a hearing device, such as a totally implantable hearing device. For purposes of illustration only, these functions will be described with reference to the systems and components described with respect to FIG. 1.

The method 100 begins at block 102 with a sound processor receiving an external sound signal transduced externally to a recipient an internal sound signal transduced internally to the recipient. The external sound signal may be the external sound signal generated by the external unit 12, while the internal sound signal may be the internal sound signal generated by the internal unit 14. The method 100 continues at block 104 with the sound processor determining that a triggering condition is present. As previously explained, the sound processor may use any suitable method, algorithm, process, or procedure, such as any known or later developed technique for identifying wind noise in a sound signal, when performing the steps of block 104.

In response to determining that the triggering condition is present, the method 100 includes (i) generating a processed sound signal that includes spectral information from at least a portion of the internal sound signal and (ii) generating a stimulation that is based on the processed sound signal, at block 106. In accordance with the above description, the sound processor may generate the processed sound signal by mixing the external sound signal and the internal sound signal and/or by including in the processed sound signal specific spectral components of the external sound signal and/or the internal sound signal.

Finally, at block 108, the method 100 then includes using the stimulation signal to stimulate the recipient. The sound processor may employ any known method, algorithm, process, or procedure to select one or more frequency bands at which to deliver a stimulus to the recipient. For instance, the sound processor may employ an N of M procedure in which a subset of frequency bands is selected from the total number of frequency bands. The sound processor may then generate electrical signals for each selected frequency band, with an amplitude of each electrical signal depending on at least the energy of an associated spectral component of the processed sound signal and recipient-specific stimulation parameters.

While various aspects and embodiments have been disclosed herein, other aspects and embodiments will be apparent to those skilled in the art. The various aspects and embodiments disclosed herein are for purposes of illustration and are not intended to be limiting, with the scope being indicated by the following claims.

What is claimed is:

1. A device configured to be implanted in a recipient, the device comprising:
   at least one audio transducer;
   a stimulation component configured to stimulate a body part in an auditory pathway of a recipient; and at least one sound processor configured for:
(i) processing a sound signal component received from the at least one audio transducer to provide an internal sound signal, wherein the internal sound signal includes spectral information indicative of an ambient sound as received at the at least one audio transducer while implanted in the recipient;
(ii) receiving from a device external to the recipient an external signal that includes information indicative of the ambient sound as received at the device external to the recipient and information indicative of an external sound signal;
(iii) determining that the external signal includes information indicative of at least one triggering condition in the ambient sound as received at the device external to the recipient; and
(iv) in response to the determining that the external signal includes information indicative of the at least one triggering condition, (a) generating a stimulation signal by (i) including in a processed sound signal one or more spectral components of the external sound signal and one or more spectral components of the internal sound signal, wherein the processed sound signal includes a plurality of spectral components, and (ii) selecting one or more spectral components from the plurality of spectral components of the processed signal, wherein the stimulation signal is based on the one or more selected spectral components, and (b) causing the stimulation component to stimulate the body part based on the stimulation signal.

2. The device of claim 1, wherein the at least one triggering condition includes the presence of a non-correlative sound being included in the ambient sound as received at the device external to the recipient.

3. The device of claim 1, wherein an amount of spectral information included in the internal sound signal that is used to generate the stimulation signal depends at least in part on a severity of the at least one triggering condition.

4. The device of claim 3, wherein the amount of spectral information varies directly with the severity of the at least one triggering condition.

5. The device of claim 1, wherein the external signal includes one or more external sound signal components, and wherein, to determine that the external signal includes information indicative of the at least one triggering condition, the at least one sound processor is further configured for (a) processing the one or more external sound signal components to provide the external sound signal, and (b) determining that the external sound signal includes the at least one triggering event.

6. The device of claim 1, wherein the external signal includes information indicative of a determination made by the device external to the recipient that the sound as received at the device external to the recipient includes the at least one triggering condition.

7. The device of claim 6, wherein the external signal further includes the external sound signal and information indicative of spectral information of the external sound signal upon which the stimulation signal is based.

8. The device of claim 1, wherein the stimulation signal is based entirely on the spectral information included in the internal sound signal.

9. A device configured to be implanted in a recipient, the device comprising:
at least one audio transducer;
a stimulation component configured to stimulate a body part in an auditory pathway of a recipient; and
at least one sound processor configured for:
(i) processing a sound signal component received from the at least one audio transducer to provide an internal sound signal, wherein the internal sound signal includes information indicative of an ambient sound as received at the at least one audio transducer while implanted in the recipient;
(ii) receiving from a device external to the recipient an external signal that includes information indicative of the ambient sound as received at the device external to the recipient and information indicative of an external sound signal;
(iii) determining that the external signal includes information indicative of at least one triggering condition in the ambient sound as received at the device external to the recipient; and
(iv) in response to the determining that the external signal includes information indicative of the at least one triggering condition, (a) generating a stimulation signal by (i) mixing the external sound signal with the internal sound signal to provide a processed sound signal, wherein the processed sound signal includes a plurality of spectral components, and (ii) selecting one or more spectral components from the plurality of spectral components, wherein the stimulation signal is based on the one or more selected spectral components, and (b) causing the stimulation component to stimulate the body part based on the stimulation signal.

10. The device of claim 9, wherein the at least one triggering condition includes the presence of a non-correlative sound being included in the ambient sound as received at the device external to the recipient.

11. The device of claim 9, wherein the one or more spectral components of the internal sound signal used to generate the stimulation signal depends at least in part on a severity of the at least one triggering condition.

12. The device of claim 11, wherein the one or more spectral components of the internal sound signal used to generate the stimulation signal varies directly with the severity of the at least one triggering condition.

13. The device of claim 9, wherein the external signal includes one or more external sound signal components, and wherein, to determine that the external signal includes information indicative of the at least one triggering condition, the at least one sound processor is further configured for (a) processing the one or more external sound signal components to provide the external sound signal, and (b) determining that the external sound signal includes the at least one triggering event.

14. The device of claim 9, wherein the external signal includes information indicative of a determination made by the device external to the recipient that the sound as received at the device external to the recipient includes the at least one triggering condition.

15. The device of claim 14, wherein the external signal further includes the external sound signal and information indicative of spectral information of the external sound signal upon which the stimulation signal is based.

16. The device of claim 9, wherein the stimulation signal is based entirely on the spectral components included in the internal sound signal.

17. A method comprising:
processing a sound signal component received from at least one audio transducer to provide an internal sound signal, wherein the internal sound signal includes information indicative of an ambient sound as received at the at least one audio transducer while implanted in a recipient;

receiving from a device external to the recipient an external signal that includes information indicative of the ambient sound as received at the device external to the recipient and information indicative of an external sound signal;

determining that the external signal includes information indicative of at least one triggering condition in the ambient sound as received at the device external to the recipient; and in response to the determining that the external signal includes information indicative of the at least one triggering condition, (a) generating a stimulation signal by (i) including in a processed sound signal one or more spectral components of the external sound signal and one or more spectral components of the internal sound signal, wherein the processed sound signal includes a plurality of spectral components, and (ii) selecting one or more spectral components from the plurality of spectral components of the processed signal, wherein the stimulation signal is based on the one or more selected spectral components, and (b) causing the stimulation component to stimulate the body part based on the stimulation signal.

18. The method of claim 17, wherein the at least one triggering condition includes the presence of a non-correlative sound being included in the ambient sound as received at the device external to the recipient.

19. The method of claim 17, wherein the one or more spectral components of the internal sound signal used to generate the stimulation signal depends at least in part on a severity of the at least one triggering condition.

20. The method of claim 19, wherein the one or more spectral components of the internal sound signal used to generate the stimulation signal varies directly with the severity of the at least one triggering condition.

21. The method of claim 17, wherein the external signal includes one or more external sound signal components, and wherein determining that the external signal includes information indicative of the at least one triggering condition further includes (a) processing the one or more external sound signal components to provide the external sound signal, and (b) determining that the external sound signal includes the at least one triggering event.

22. The method of claim 17, wherein the external signal includes information indicative of a determination made by the device external to the recipient that the sound as received at the device external to the recipient includes the at least one triggering condition.

23. The method of claim 22, wherein the external signal further includes the external sound signal and information indicative of spectral information of the external sound signal upon which the stimulation signal is based.

24. The method of claim 17, wherein the stimulation signal is based entirely on the spectral components included in the internal sound signal.

* * * * *